United States Patent

Hammond et al.

(10) Patent No.: US 6,474,137 B1
(45) Date of Patent: Nov. 5, 2002

(54) MEASURING RELATIVE DENSITY OF A GAS

(75) Inventors: Paul Stephen Hammond, Ashby De La Zouch; Robert Richard Thurston, Melbourne, both of (GB)

(73) Assignee: Lattice Intellectual Property Limited, London (GB)

( * ) Notice: Subject to any disclaimer, the term of this patent is extended or adjusted under 35 U.S.C. 154(b) by 0 days.

(21) Appl. No.: 09/462,102

(22) PCT Filed: Jul. 17, 1998

(86) PCT No.: PCT/GB98/02136

§ 371 (c)(1),
(2), (4) Date: Feb. 3, 2000

(87) PCT Pub. No.: WO99/05517

PCT Pub. Date: Feb. 4, 1999

(30) Foreign Application Priority Data

Jul. 22, 1997 (GB) ............................................... 9715448

(51) Int. Cl.$^7$ ............................................... G01N 29/02
(52) U.S. Cl. ...................................... 73/24.05; 73/24.01
(58) Field of Search ............................. 73/24.01, 24.05, 73/24.02, 23.32, 30.01

(56) References Cited

U.S. PATENT DOCUMENTS

| | | | | |
|---|---|---|---|---|
| 3,381,520 A | * | 5/1968 | Bouquard et al. | 73/24.01 |
| 3,789,655 A | * | 2/1974 | Passeri | 73/24.01 |
| 4,246,773 A | * | 1/1981 | Haruta | 73/24.01 |
| 4,283,256 A | * | 8/1981 | Howard et al. | 73/23.32 |
| 4,442,700 A | | 4/1984 | Swoboda | |
| 5,265,458 A | * | 11/1993 | Usami et al. | 73/23.32 |
| 5,285,675 A | * | 2/1994 | Colgate et al. | 73/23.2 |
| 5,325,703 A | * | 7/1994 | Magori | 73/23.32 |
| 5,333,591 A | * | 8/1994 | Korsmeier et al. | 73/23.32 |
| 5,467,637 A | * | 11/1995 | Hasegawa et al. | 73/24.01 |
| 5,537,854 A | * | 7/1996 | Phillips et al. | 73/24.01 |
| 5,697,346 A | * | 12/1997 | Beck | 73/23.31 |
| 6,209,387 B1 | * | 4/2001 | Savidge | 73/23.29 |

FOREIGN PATENT DOCUMENTS

| | | |
|---|---|---|
| EP | 0 012 788 | 7/1980 |
| GB | 2 050 605 | 1/1981 |
| GB | 2 309 524 | 7/1997 |
| WO | WO 87/02770 | 5/1987 |

\* cited by examiner

*Primary Examiner*—Daniel S. Larkin
*Assistant Examiner*—Michael Cygan
(74) *Attorney, Agent, or Firm*—Oblon, Spivak, McClelland, Maier & Neustadt, P.C.

(57) ABSTRACT

A method and apparatus for measuring the relative density of a gas, for example natural gas. The gas is supplied through an inlet to a chamber and is output through an outlet. Using a control and an ultra-sonic transducer emitter and an ultra-sonic transducer receiver, the speed of sound in the gas corrected to standard conditions is calculated. Then, the control operates to measure the relative density RD of the gas using the formula $$RD = a \times SoSsc + b,$$

where SoSsc is the speed of sound in the gas corrected to standard conditions, and a and b are constants.

18 Claims, 3 Drawing Sheets

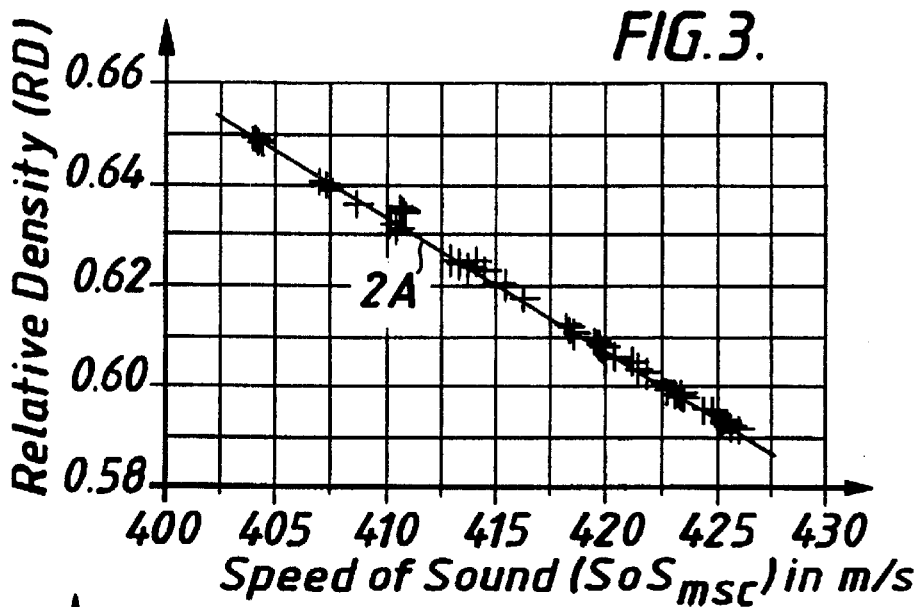
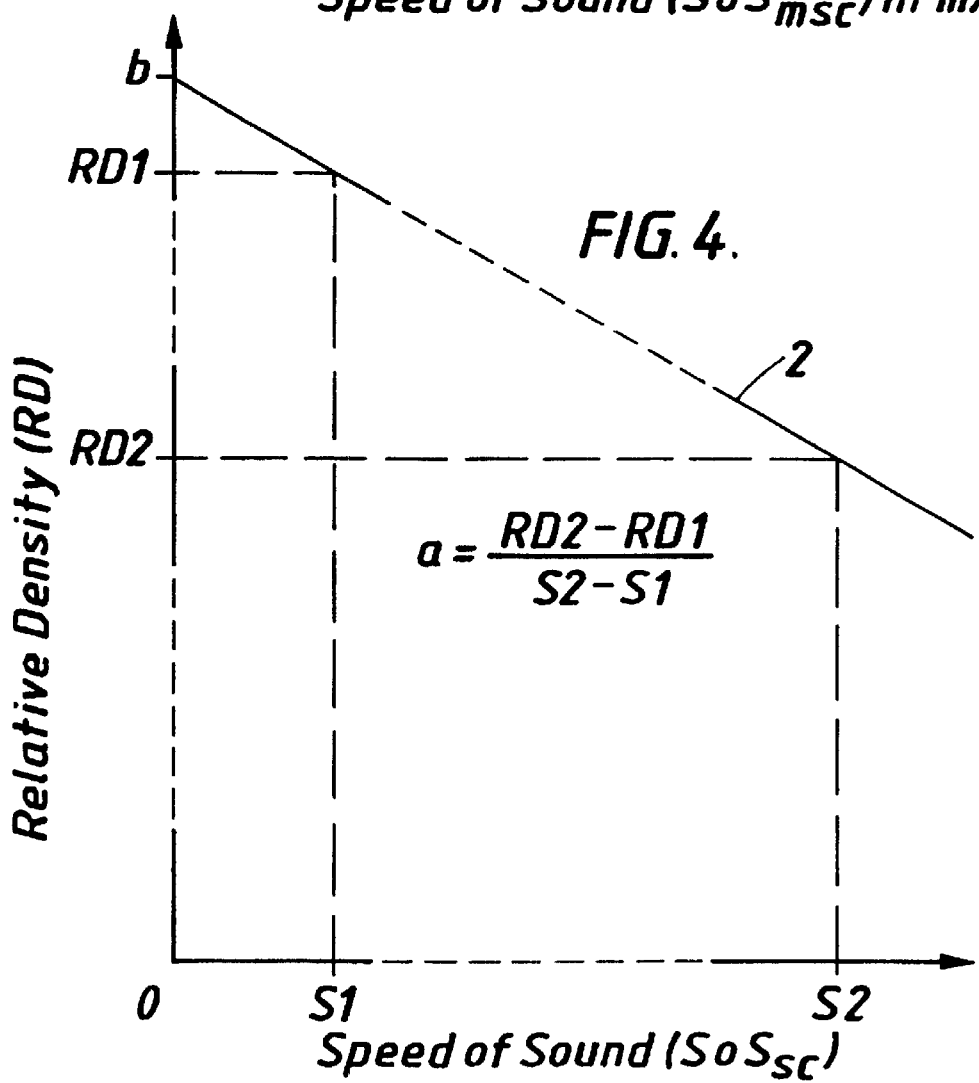

MEASURING RELATIVE DENSITY OF A GAS

This invention relates to a method and apparatus to measure relative density of a gas.

BACKGROUND OF THE INVENTION

The gas may be fuel gas, for example natural gas.

SUMMARY OF THE INVENTION

According to a first aspect of the invention a method of measuring the relative density of a gas comprises making a measure of the speed of sound in the gas and using the speed of sound in an operation producing the relative density of the gas corresponding to said speed of sound.

Said method may comprise making a measure of the speed of sound in the gas corrected to standard conditions and obtaining the relative density by a procedure involving use of the formula $$RD = a \times SoSsc + b,$$

where RD is the relative density of the gas, SoSsc is the speed of sound in the gas corrected to standard conditions (sc), and a and b are constants.

The speed of sound in the gas may be corrected to metric standard conditions (msc) whereby the formula may be written as $$RD = a \times SoSsc + b,$$

According to a second aspect of the invention apparatus to measure the relative density of a gas comprises means to measure the speed of sound in the gas, and means to use the speed of sound in an operation producing the relative density of the gas corresponding to said speed of sound.

Said apparatus may comprise means to measure the speed of sound SoSsc in the gas corrected to standard conditions, and means to obtain the relative density by a procedure involving use of the formula $$RD = a \times SoSsc + b,$$

In said apparatus the speed of sound may be corrected to standard metric conditions.

The method and apparatus may be adapted to use a measure of the calorific value of the gas to calculate the Wobbe Index of the gas using the formula $$WI = \frac{CV}{\sqrt{RD}},$$

where WI is the Wobbe Index and CV is the calorific value of the gas.

BRIEF DESCRIPTION OF THE DRAWINGS

Each aspect of the invention will now be further described, by way of example, with reference to the accompanying drawings in which:

FIG. 3 is a graph illustrating a substantially linear relationship of variation of speed sound (SoSmsc) in metres per second (m/s) in natural gas corrected to metric standard conditions (msc) with respect to variation in relative density (RD) of the natural gas, in which the natural gas concerned is of a kind typically supplied in the United Kingdom to consumers via gas mains;

FIG. 4 is graph illustrating diagrammatically and in a general sense a substantially linear relationship of variation of speed of sound (SoSsc)in a gas corrected to standard conditions (sc) with respect to variation in relative density (RD) of the gas, and which graph can be used to illustrate how values for the constants a and b may be derived.

DESCRITPION OF THE PREFERRED EMBODIMENTS

With reference to the drawings, in which like references refer to like or comparable parts, FIG. 4 shows a linear relationship 2 discovered by the inventors between variations in the speed of sound in a gas corrected to standard conditions with variation of the relative density of the gas. Standard conditions for gases are known and may be of various types, for example normal temperature and pressure (ntp) or metric standard conditions (msc). The linear relationship 2 in FIG. 4 is expressed by the formula $$RD = a \times SoSsc + b,$$

in which RD is the relative density of the gas, SOSsc is the speed of sound in the gas corrected to standard conditions, a is the slope or gradient of the linear relationship 2 and b is the value of the relative density when the speed of sound in the gas corrected to standard conditions is zero. Relative density is a dimensionless number.

To establish the relationship shown in FIG. 4 for a gas of interest the different relative densities of a gas of variable relative density is measured using any suitable known method, for example, by chromatography using chromatographs or densionmeters, and at each relative density a measurement is made of the speed of sound in the gas corrected to standard conditions. Those values of the speed of sound and their corresponding relative density values are plotted to give the relationship 2 from which the constants a and b can be obtained.

In FIG. 3 a linear relationship 2A is illustrated showing the variation of the speed of sound SoSmsc in natural gas in metres per second with variation in relative density of the natural gas. The speed of sound in FIG. 3 is corrected to standard metric conditions (msc). Standard metric conditions are a temperature of 15 degrees Celsius and a pressure of 1.01325 barA. Using the linear relationship 2A in FIG. 3 the value of the constant a is −0.002608, and the value of the constant b is 1.70245, so for natural gas the relative density RD can be derived from the formula $$RD = -0.002608 \times SoSmsc + 1.70245 \qquad (II).$$

It is possible to derive a linear relationship 2 (FIG. 4) for any suitable gas, including any suitable fuel gas.

Figure 1:
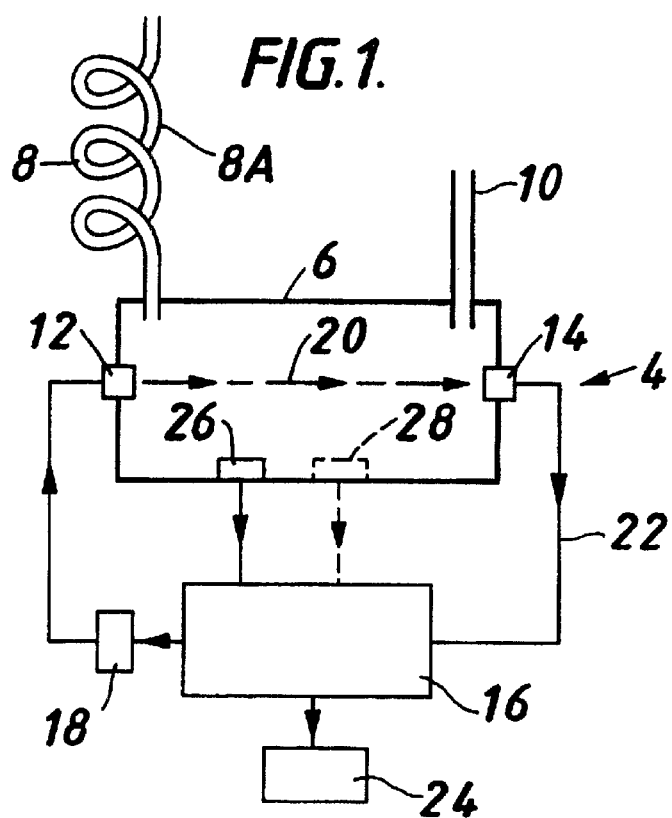
FIG. 1 is a diagrammatic example of an embodiment of apparatus to measure the relative density of a gas according to a second aspect of the invention using the method according to the first aspect of the invention.

With reference to FIG. 1 an apparatus 4 to measure the relative density RD of a gas using the formula at (I) above has a chamber 6 into which the gas is supplied through inlet conduit 8 and leaves through an outlet conduit 10. The inlet conduit includes heat exchange means 8A, for example a copper coil, by which the temperature of the incoming gas can be adjusted to a value substantially the same as that of the ambient temperature whereby the gas in the chamber 6 is of substantially uniform temperature therethroughout. The chamber 6 includes an ultra-sound emitter transducer 12 and an ultra-sound receiver transducer 14. An electronic control means 16 including computer means is connected to a signal generator 18 so that under control of the control means 16 the signal generator causes the transducer 12 to emit ultra-sound signals 20 as desired. The ultra-sound signals 20 are received by the transducer 14 and their reception is signalled to the control means 16 via line 22. The time of flight of the ultra-sonic signals between transducers 12 and 14 is measured by the control means 16 which is arranged to calculate the speed of sound SoSsc in the gas chamber 6. Using the formula (I) above, the value of the relative density RD of the gas can be calculated and may be visually displayed and/or printed or otherwise recorded by recording means 24 in response to signals from the control means 16.

An alternative technique may be to provide the control means 16 with a pre-determined look-up table in which various values of relative density are co-related to respective speed of sound values corrected to standard conditions. The control means 16 chooses which speed of sound value in the look-up table is closest to the measured speed of sound in the gas using the transducers 12 and 14 and thus identifies the corresponding relative density value which is the same as or closest to the actual relative density value of the gas.

In order that the control means 16 can calculate the speed of sound corrected to the desired standard conditions, a temperature sensor 26 in the chamber 6 provides the control means with data representing the value of the temperature of the gas in the chamber.

To a first approximation the speed of sound is dependent only on changes in ambient temperature and not in pressure. So, if desired, information relating to the gas pressure in the chamber 6 need not be provided for the calculation of the speed of sound corrected to standard conditions; it being assumed that the gas pressure has a substantially constant value. However a pressure sensor 28 may be provided to send gas pressure measurement data to the control means 16 for use in the corrected speed of sound calculation.

The gas may be any gas, for example any fuel gas. In the case of natural gas or methane the control means 16 may use the formula at (II) above to obtain the value of relative density RD.

Figure 2:
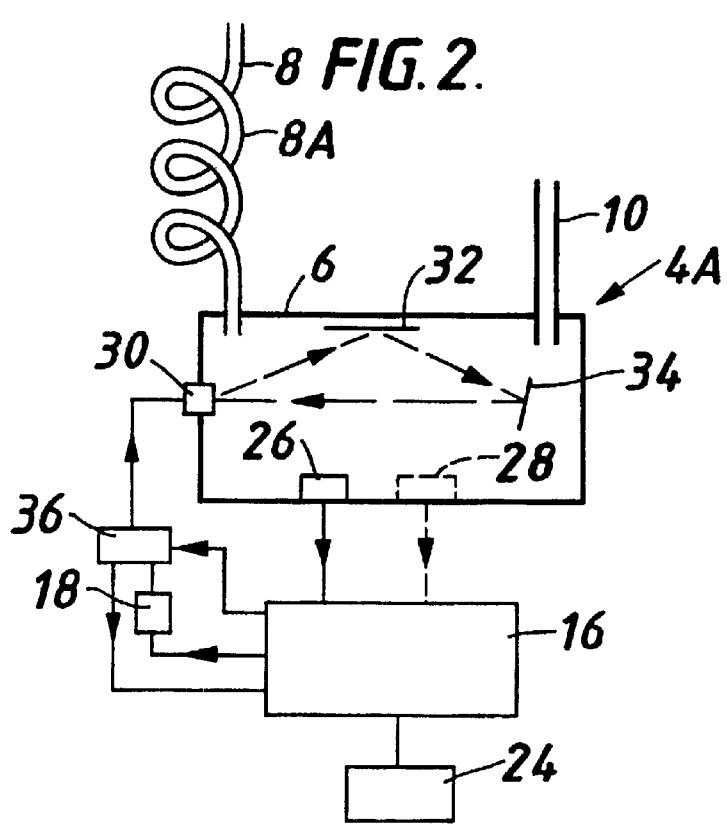
FIG. 2 is a diagrammatic example of another embodiment of apparatus to measure the relative density of a gas according to the second aspect of the invention using the method according to the first aspect of this invention.

In apparatus 4A in FIG. 2 there is a single ultrasonic transducer emitter-receiver 30 from which ultra-sonic signals are emitted for reflection off reflectors 32 and 34 back to the transducer 30. The length of the path between emission and reception is known. The electronic control means 16 can operate a switching device 36 and the signal generator 18. When the transducer 30 is to emit an ultra-sonic signal the control means 16 actuates the switching device 36 to one state to pass signals from the signal generator 18 to drive the transducer 30 as an emitter. Then the control means 16 actuates the switching device 36 to another state to allow data indicating reception of the reflected ultra-sonic signal by the transducer 30 to pass to the control means 16 which can thus measure the time of flight of the ultra-sonic signal in the chamber 6 and thus the speed of sound in the gas.

Any suitable method may be used to measure the speed of sound such as that disclosed in U.S. Pat. No. 4,938,066. However, the most preferable method is that disclosed in UK patent application Nos. GB 9813509.8, GB 9813513.0 and GB 9813514.8.

By any suitable technique known per se the control means 16 may be provided with information representing the calorific value of the gas or the control means may be provided with information enabling it to calculate the calorific value CV of the gas. Then the control means 16 may calculate or otherwise obtain the value of the Wobbe Index WI of the gas by use of the formula $$WI = \frac{CV}{\sqrt{RD}}.$$

When fuel gas is combusted in a process (e.g. furnace, kiln, compressor, engine etc.) some form of control system is used to set the oxygen (in this case in the form of air)/fuel gas ratio to ensure optimum combustion. An allowance is made in the amount of excess air to account in part, for variations in fuel gas composition changes. This allowance means that the process is running less efficiently than it could do because extra air is being heated and vented.

However, a measure of the relative density or Wobbe Index, which is indicative of the fuel gas quality and which may be found according to the present invention, may be used in a feed forward control strategy to improve the accuracy of control available and achieve better efficiency.

Figure 5:
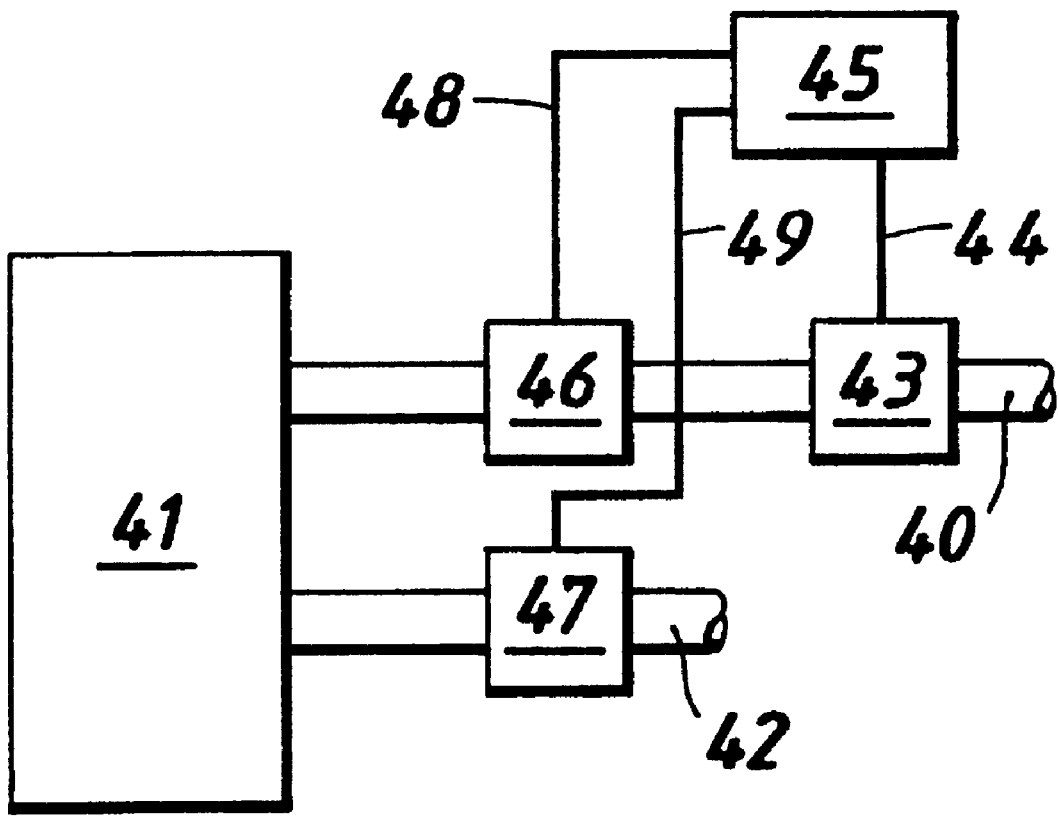
FIG. 5 is a diagrammatic example of a feed forward air/fuel gas control system utilising the present invention.

An apparatus to perform such control is shown in FIG. 5. Fuel gas is supplied via a conduit 40, such as a pipe, to a gas fired process 41 such as a furnace, kiln, a compressor or an engine and oxygen in the form of air is supplied to the process 41 via another conduit 42. Any suitable speed of sound measuring device 43 which may be in the form a probe temporarily insertable into the conduit 40 or as a permanent fixture is arranged to measure the speed of sound of the fuel gas passing through the conduit 40. The speed of sound of the fuel gas measured by device 43 is passed via a connection 44 to a control means 45, which may be a microprocessor or a computer for example. Control means 45 determines the relative density of the fuel gas from the received speed of sound measurement from device 43 as explained earlier. Having determined a measure of the gas quality, the control means is able to adjust the air/fuel gas ratio setpoint using an oxygen/fuel gas ratio control system 46, 47 to achieve better efficiency. In this case the oxygen/fuel gas ratio control system comprises two variable opening valves 46, 47 one in each of the fuel gas and air conduits 40, 42 respectively and both controlled by the control means 45 via connections 48, 49. Alternatively the oxygen/fuel gas control system could comprise a variable opening valve on just one of conduits 40, 42.

What is claimed is:

1. A method of determining a relative density of a gas comprising:

precalculating a slope and an intercept of a linear relationship, between the relative density and a speed of sound, by taking a predetermined number of measurements of an initial relative density and a corresponding initial speed of sound in the gas;

measuring the speed of sound in the gas; and calculating the relative density of the gas from the linear relationship using the slope, the intercept and the corresponding measured speed of sound.

2. A method as claimed in claim 1, wherein the measured speed of sound in the gas is corrected to standard conditions, and the relative density is obtained by a procedure involving a formula $$RD = a \times SoSsc + b,$$

where RD is the relative density of the gas, SoSsc is the speed of sound in the gas corrected to standard conditions (sc), and a and b are respectively the slope and intercept.

3. A method as claimed in claim 1, wherein the linear relationship is $$RD = a \times SoSsc + b,$$

where SoSsmc is a speed of sound in the gas corrected to metric standard conditions.

4. A method as claimed in claim 3, wherein the linear relationship for the relative density RD of the gas has the slope a being substantially −0.002608, the intercept b being substantially 1.70245, and the speed of sound in the gas corrected to metric standard conditions SoSsmc being in units of meters per second.

5. A method as claimed in claim 2, wherein during the predetermined number of measurements of corrected speeds of sound in the gas, the gas pressure is assumed substantially the same for all said successive measurements.

6. A method as claimed in claim 1, wherein a Wobbe Index WI of is measured using the formula $$WI = \frac{CV}{\sqrt{RD}},$$

where CV is a calorific value of the gas and RD is the relative density.

7. An engine comprising:
   means for receiving a supply of oxygen;
   means for receiving a supply of fuel gas;
   an oxygen/fuel gas ratio control system;
   control means for adjusting an oxygen/fuel gas ratio of a gas fired process, comprising,
      means for precalculating a slope and an intercept of a linear relationship between a relative density and a speed of sound,
      means for measuring the speed of sound in the oxygen/fuel gas, and
      means for using a measured speed of sound for determining the relative density of a fuel gas for the gas fired process; and
      means for adjusting an oxygen/fuel gas ratio control system for the gas fired process in accordance with the determined relative density,
   wherein said control means is programmed to precalculate the slope and the intercept of the linear relationship between the relative density and the speed of sound by taking a predetermined number of measurements over an initial relative density and a corresponding initial speed of sound in the gas,
   wherein said control means is programmed to measure the speed of sound in the gas, and
   wherein said control means is programmed to calculate the relative density of the gas from the linear relationship using the slope, the intercept and the corresponding measured speed of sound.

8. An apparatus for measuring a relative density of a gas, comprising:
   means for precalculating a slope and an intercept of a linear relationship between the relative density and a speed of sound;
   eans tor measuring the speed of sound in the gas; and
   means for calculating the relative density of the gas,
   wherein said apparatus is programmed to precalculate the slope and the intercept of the linear relationship between the relative density and the speed of sound by taking a predetermined number of measurements over an initial relative density and a corresponding initial speed of sound in the gas,
   wherein said apparatus is programmed to measure the speed of sound in the gas, and
   wherein said apparatus is programmed to calculate the relative density of the gas from the linear relationship using the slope, the intercept and the corresponding measured speed of sound.

9. The apparatus as claimed in claim 8, further comprising:
   correcting means for correcting the measured speed of sound in the gas to standard conditions,
   wherein said correcting means uses the measured speed of sound and the linear relationship $$RD = a \times SoSsc + b,$$

for producing the relative density of the gas,
   where RD is the relative density of the gas, SoSsc is a speed of sound in the gas corrected to standard conditions (sc), and a and b are respectively the slope and intercept.

10. The apparatus as claimed in claim 8, wherein the linear relationship is $$RD = a \times SoSsc + b,$$

where SoSsmc is a speed of sound in the gas corrected to metric standard conditions (smc), and a and b are respectively the slope and intercept.

11. The apparatus as claimed in claim 10, wherein linear relationship for the relative density RD of the gas has the slope a being substantially −0.002608, the intercept b being substantially 1.70245, and the speed of sound in the gas corrected to standard metric conditions SoSsmc being in units of meters per second.

12. The apparatus as claimed in claim 9, wherein during the predetermined number of measurements of corrected speeds of sound in the gas, the gas pressure is assumed substantially the same for all said successive measurements.

13. The apparatus as claimed in claim 8, wherein the gas is supplied through a heat exchanger to a region in which an ultra-sonic signal is emitted for the measurement of the speed of sound in the gas.

14. An apparatus as claimed in claim 8, comprising:
   means for calculating a Wobbe Index WI using a formula $$WI = \frac{CV}{\sqrt{RD}},$$

where CV is a calorific value of the gas, RD is the relative density of the gas; and
   means for receiving and/or computing and/or deriving the calorific value CV of the gas.

15. The apparatus as claimed in claim 8, further comprising:
   control means for adjusting the oxygen/fuel gas ratio of a gas fired process comprising an apparatus configured to measure the relative density of a fuel gas for the gas fired process; and
   means for adjusting an oxygen/fuel gas ratio control system for the gas fired process in accordance with the determined relative density.

16. A furnace comprising:
   means for receiving a supply of oxygen;
   means for receiving a supply of fuel gas;
   an oxygen/fuel gas ratio control system;

control means for adjusting an oxygen/fuel gas ratio of gas fired process, comprising,
- means for precalculating a slope and an intercept of a linear relationship between a relative density and a speed of sound,
- means for measuring the speed of sound in the oxygen/fuel gas, and
- means for using a measured speed of sound for determining the relative density of a fuel gas for the gas fired process; and
- means for adjusting the oxygen/fuel gas ratio control system for the gas fired process in accordance with the determined relative density,
- wherein said control means is programmed to precalculate the slope and the intercept of the linear relationship between the relative density and the speed of sound by taking a predetermined number of measurements over an initial relative density and a corresponding initial speed of sound in the gas,
- wherein said control means is programmed to measure the speed of sound in the gas, and
- wherein said control means is programmed to calculate the relative density of the gas from the linear relationship using the slope, the intercept and the corresponding measured speed of sound.

17. A kiln comprising:

means for receiving a supply of oxygen;

means for receiving a supply of fuel gas;

an oxygen/fuel gas ratio control system;

control means for adjusting an oxygen/fuel gas ratio of a gas fired process, comprising,
- means for precalculating a slope and an intercept of a linear relationship between a relative density and a speed of sound,
- means for measuring the speed of sound in the oxygen/fuel gas, and
- means for using a measured speed of sound for determining the relative density of a fuel gas for the gas fired process; and
- means for adjusting an oxygen/fuel gas ratio control system for the gas fired process in accordance with the determined relative density,
- wherein said control means is programmed to precalculate the slope and the intercept of the linear relationship between the relative density and the speed of sound by taking a predetermined number of measurements over an initial relative density and a corresponding initial speed of sound in the gas,
- wherein said control means is programmed to measure the speed of sound in the gas, and
- wherein said control means is programmed to calculate the relative density of the gas from the linear relationship using the slope, the intercept and the corresponding measured speed of sound.

18. A compressor comprising:

means for receiving a supply of oxygen;

means for receiving a supply of fuel gas;

an oxygen/fuel gas ratio control system;

control means for adjusting an oxygen/fuel gas ratio of a gas fired process, comprising,
- means for precalculating a slope and an intercept of a linear relationship between a relative density and a speed of sound,
- means for measuring the speed of sound in the oxygen/fuel gas, and
- means for using a measured speed of sound for determining the relative density of a fuel gas for the gas fired process; and
- means for adjusting an oxygen/fuel gas ratio control system for the gas fired process in accordance with the determined relative density,
- wherein said control means is programmed to precalculate the slope and the intercept of the linear relationship between the relative density and the speed of sound by taking a predetermined number of measurements over an initial relative density and a corresponding initial speed of sound in the gas,
- wherein said control means is programmed to measure the speed of sound in the gas, and
- wherein said control means is programmed to calculate the relative density of the gas from the linear relationship using the slope, the intercept and the corresponding measured speed of sound.

\* \* \* \* \*